United States Patent
Jun

(10) Patent No.: US 11,977,812 B2
(45) Date of Patent: May 7, 2024

(54) AUTOMATIC SPEECH RECOGNIZER AND SPEECH RECOGNITION METHOD USING KEYBOARD MACRO FUNCTION

(71) Applicant: PUZZLE AI CO., LTD., Seoul (KR)

(72) Inventor: Ha Rin Jun, Daejeon (KR)

(*) Notice: Subject to any disclaimer, the term of this patent is extended or adjusted under 35 U.S.C. 154(b) by 116 days.

(21) Appl. No.: 17/772,962

(22) PCT Filed: Aug. 5, 2020

(86) PCT No.: PCT/KR2020/010359
§ 371 (c)(1),
(2) Date: Apr. 28, 2022

(87) PCT Pub. No.: WO2021/085811
PCT Pub. Date: May 6, 2021

(65) Prior Publication Data
US 2022/0391162 A1    Dec. 8, 2022

(30) Foreign Application Priority Data
Oct. 29, 2019    (KR) .......................... 10-2019-0135488

(51) Int. Cl.
*G06F 3/048*        (2013.01)
*G06F 3/023*        (2006.01)
(Continued)

(52) U.S. Cl.
CPC ................ *G06F 3/16* (2013.01); *G06F 3/023* (2013.01); *G10L 15/26* (2013.01)

(58) Field of Classification Search
CPC ............. G06F 3/16; G06F 3/023; G10L 15/26
See application file for complete search history.

(56) References Cited

U.S. PATENT DOCUMENTS

| 6,578,007 B1 * | 6/2003 | Howes ............. G06Q 10/06315 705/7.22 |
| 8,452,594 B2 * | 5/2013 | Oz ........................ G06F 40/174 715/224 |

(Continued)

FOREIGN PATENT DOCUMENTS

| JP | H11-244321 | 9/1999 |
| JP | 2001-101162 A | 4/2001 |

(Continued)

OTHER PUBLICATIONS

Johnson et al., A systematic review of speech recognition technology in health care, 2014, BioMed Central, 14 pages.*

(Continued)

*Primary Examiner* — Linh K Pham
(74) *Attorney, Agent, or Firm* — ANTONIO HA & U.S. PATENT, LLC

(57) ABSTRACT

The present invention relates to an automatic speech recognizer and a speech recognition method using a keyboard macro function, the method being characterized by including the steps in which: a transcription data generation unit generates transcription data on the basis of speech data input through a microphone; a labeling unit, in order to perform a macro function on the generated transcription data, labels and sessionizes the generated transcription data and stores the labeled and sessionized data when a preset labeling target word is included; and the generated transcription data is displayed in a space in a utility program in which data can be input by a virtual keyboard.

6 Claims, 3 Drawing Sheets

(51) Int. Cl.
*G06F 3/16* (2006.01)
*G10L 15/26* (2006.01)

(56) References Cited

U.S. PATENT DOCUMENTS

| | | | |
|---|---|---|---|
| 9,514,740 B2 * | 12/2016 | Jost | G10L 15/063 |
| 2002/0087357 A1 * | 7/2002 | Singer | G16H 10/60 |
| | | | 704/E15.045 |
| 2006/0200354 A1 | 9/2006 | Ito et al. | |
| 2009/0089100 A1 * | 4/2009 | Nenov | G10L 15/22 |
| | | | 704/235 |
| 2009/0187407 A1 | 7/2009 | Soble et al. | |
| 2014/0142939 A1 | 5/2014 | Aradi et al. | |
| 2014/0324477 A1 * | 10/2014 | Oez | G06Q 50/22 |
| | | | 705/3 |
| 2016/0162642 A1 * | 6/2016 | Atkinson | G03H 1/0005 |
| | | | 705/3 |
| 2019/0121532 A1 | 4/2019 | Strader et al. | |
| 2019/0122144 A1 * | 4/2019 | Kabeya | H04L 63/1408 |
| 2019/0258704 A1 | 8/2019 | Mertens et al. | |
| 2021/0090694 A1 * | 3/2021 | Colley | G16H 15/00 |

FOREIGN PATENT DOCUMENTS

| | | |
|---|---|---|
| JP | 2004-530205 A | 9/2004 |
| JP | 2005-027978 A | 2/2005 |
| JP | 2005-192024 A | 7/2005 |
| JP | 2006-223357 A | 8/2006 |
| JP | 2008-203516 A | 3/2010 |
| JP | 2012-140189 A | 7/2012 |
| JP | 2016-102920 A | 6/2016 |
| JP | 2017-182075 A | 10/2017 |
| KR | 10-0354365 | 9/2002 |
| KR | 10-2003-0025507 | 3/2003 |
| KR | 10-0778966 | 11/2007 |
| KR | 10-2014-0061047 | 5/2014 |
| KR | 10-2017-0006369 | 1/2017 |
| KR | 10-1955225 | 3/2019 |

OTHER PUBLICATIONS

English Specification of 10-0354365.
English Specification of 10-1955225.
English Specification of 10-2017-0006369.
English Specification of JP2001-101162A.
English Specification of 10-2003-0025507.
English Specification of 10-2014-0061047.
English Specification of JP2005-027978A, 2005.
English Specification of JP2012-140189A ,2012.
English Specification of JP2004-530205A, 2004.
English Specification of JP2005-192024A, 2005.
English Specification of JP2006-223357A, 2006.
English Specification of JP2008-203516A, 2010.
English Specification of JP2016-102920A, 2016.
English Specification of JP2017-182075A, 2017.
English Specification of JPH11-244321, 1999.
English Specification of 10-0778966, 2007.

* cited by examiner

AUTOMATIC SPEECH RECOGNIZER AND SPEECH RECOGNITION METHOD USING KEYBOARD MACRO FUNCTION

TECHNICAL FIELD

The present invention relates to an automatic speech recognizer and automatic speech recognition method and, more specifically, to a medical automatic speech recognizer and automatic speech recognition method using a keyboard macro function to transcribe speech data and perform a labeling task.

BACKGROUND ART

The conventional EMR (Electronic Medical Record) system has the advantage that all of the patient's medical records are entered and managed electronically, but the work of the medical staff is focused on recording rather than the patient's treatment.

However, there is a situation in which the doctor has to look at the computer screen to enter medical records, rather than the patient, during treatment.

In particular, it is difficult to use the mouse/keyboard when the hands cannot be used during treatment, such as in the operating room or clinical pathology department and, thus, separate manipulation is required to simultaneously perform treatment of the patient and creation of medical records and, to that end, an assistant's help is required.

Meanwhile, Korean Patent No. 354,365, titled "Interactive computer control display system with speech command input recognition function and method for providing speech command input to the system," discloses an Interactive computer control display system with a speech command input recognition function and a method for providing speech command input to the system, which relates to an interactive computer controlled display system for speech command input recognition and visual feedback, in which the system includes a means to previously determine multiple speech commands to respectively initiate multiple corresponding system operations and a means to provide an associated set of speech terms respectively associated with the multiple commands.

In this case, each term has a relevance to its associated command and includes a means for detecting the speech command and the speech term and provides a means for displaying the command in response to detection of the speech command and a means for displaying the related command in response to the detected speech term having a relevance to one of the commands.

There are ongoing efforts to develop technology for recognizing a speech and providing a function according to the speech command.

DETAILED DESCRIPTION OF THE INVENTION

Technical Problems

The present invention has been conceived in light of the foregoing background and aims to provide a convenient automatic speech recognizer and automatic speech recognition method for recording speech directly in the form of text in a context where it is difficult to use hands for medical records, e.g., electronic medical records or surgery records, during actual patient treatment in the medical field.

There is also provided an automatic speech recognizer and automatic speech recognition method that enables transcription of speech, as text, to the input field of the recording system in the medical field, through the speech recognizer which is always active, and search for necessary information or command execution only with speech input through a keyboard macro input device without a separate keyboard or mouse, thus increasing efficiency of information processing.

Means to Address the Problems

To achieve the above objectives, the present invention includes the following components.

In other words, according to an embodiment of the present invention, an automatic speech recognition method, performed on an automatic speech recognizer using the keyboard macro function, comprises the steps of generating transcription data based on speech data input through a microphone by a transcription data generation unit and labeling, sessionizing and storing the generated transcription data if the generated transcription data includes a preset labeling target word for performing a macro function, by a labeling unit.

According to an aspect of the present invention, the automatic speech recognition method further comprises the step of invoking the transcription data, sessionized and stored in the sessionizing and storing step, and performing, by macro execution unit, an operation according to the macro function if the generated transcription data includes the preset labeling target word.

Meanwhile, an automatic speech recognizer using a keyboard macro function comprises a transcription data generation unit generating transcription data based on speech data input through a microphone and a labeling unit labeling, sessionizing and storing the generated transcription data if the transcription data generated by the transcription data generation unit includes a preset labeling target word for performing a macro function.

According to an aspect of the present invention, the automatic speech recognizer further comprises a macro execution unit invoking the transcription data, sessionized by the labeling unit, and performing an operation according to the macro function if the transcription data generated by the transcription data generation unit includes the preset labeling target word.

Effects of the Invention

According to the present invention, it is possible to provide a convenient automatic speech recognizer and automatic speech recognition method for recording speech directly in the form of text in a context where it is difficult to use hands for medical records, e.g., electronic medical records or surgery records, during actual patient treatment in the medical field.

By the automatic speech recognizer and automatic speech recognition method using a keyboard macro function according to the present invention, it is possible to provide an automatic speech recognizer and automatic speech recognition method that enables transcription of speech, as text, to the input field of the recording system in the medical field, through the speech recognizer which is always active, and search for necessary information or command execution only with speech input through a keyboard macro input device without a separate keyboard or mouse, thus increasing efficiency of information processing.

Specifically, it is possible to enable recording of medical information directly through speech, without limitation in environment, in a context where it is impossible to manipulate a separate mouse and keyboard such as during surgery in the operating room, thus increasing the accuracy of information and concentration on the patient's treatment or operation.

It is also possible to increase convenience and time efficiency for medical doctors by replacing the input type with speech input in the medical environment where a sufficient time is not allowed for the doctor to input medical records while treating the patient.

MODE TO PRACTICE THE INVENTION

Hereinafter, preferred embodiments of the present invention are described in detail with reference to the accompanying drawings.

Figure 1:
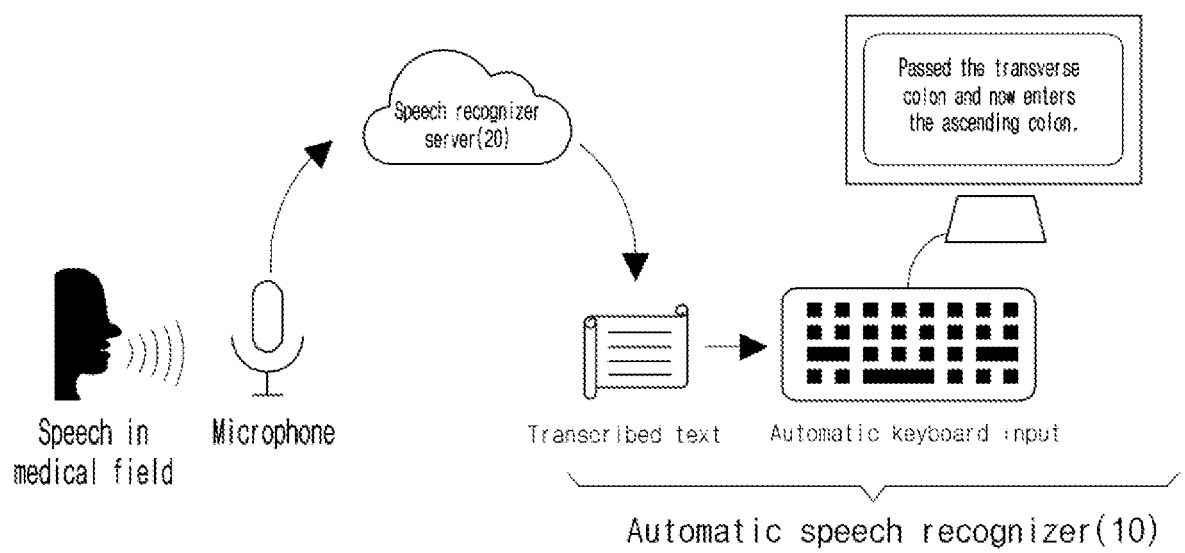
FIG. 1 is an example view illustrating operations of a medical automatic speech recognizer using a keyboard macro function according to an embodiment of the present invention.

FIG. 1 is an example view illustrating operations of a medical automatic speech recognizer using a keyboard macro function according to an embodiment of the present invention.

As shown in FIG. 1, according to an embodiment, an automatic speech recognizer 10 using a keyboard macro function receives a speech message through a microphone in the medical field. Then, the automatic speech recognizer 10 generates transcription data based on the speech data while communicating with a speech recognizer server 20.

In this case, the speech recognizer server 20 includes a platform providing a medical automatic speech recognition service according to an embodiment. The speech recognizer server 20 may provide the automatic speech recognizer 10 with basic information necessary for transcribing speech data.

The automatic speech recognizer 10 automatically performs a keyboard input function based on the transcription data. In other words, the automatic speech recognizer 10 according to an embodiment may perform operations or functions according to the transcription data by the keyboard macron input device function even without input of a control signal of an actual physical keyboard or mouse.

According to the present invention, the automatic speech recognizer 10 transcribes the speech input through the speech recognizer server 20, used for an input field of a recording system in the medical field, as text, and the text is automatically input and stored through a keyboard macro input device without use of a separate mouse or keyboard.

As an example, capture position information among the content of the speech, may be separately labeled and stored in a session, and if a request for the capture position or specific information is made by speech, information related to the capture position may be highlighted and displayed or may be fed back as speech, and modification and input processing on a blank (e.g., variable value) in the speech template is also possible.

Further, according to an embodiment, the automatic speech recognizer 10 may transcribe the recognized speech to a data inputtable space on various utility programs, such as a notepad, chatting program, HWP or Word, or Excel, as well as the electronic medical record (EMR) program, and output it in the form of text.

Conventionally, speech-recognized, transcribed text-type information is scraped, copied, and pasted into a required area by a mouse. However, the automatic speech recognizer 10 according to an embodiment of the present invention directly converts the speech-recognized content into text in such a manner as to be input by a virtual keyboard and output it on the screen, so that it is possible to output it on the screen as if it is directly input on the program by a keyboard.

Accordingly, it is possible to provide the advantage that the range of programs to which the transcribed content is applicable is increased in displaying the speech, recognized by the automatic speech recognizer 10, in the form of text.

Accordingly, the automatic speech recognizer 10 according to an embodiment may input the result, obtained via speech recognition on the input field, as if it is actually input by a keyboard, without separate interaction, if there is an input field regardless of the type of the EMR program in the medical industry.

Further, the automatic speech recognizer 10 according to an embodiment may be applied to medical image storage system (PACS) and various medical programs as well as the electronic medical record (EMR) program.

According to an embodiment, the automatic speech recognizer 10 is an IP-assigned terminal and performs network communication with the speech recognizer server 20 through, e.g., the Internet. For example, the automatic speech recognizer 10 may be a desktop PC, a slate PC, a laptop computer, a PMP (Portable Multimedia Player), an Ultrabook, a wearable device (e.g., a watch-type terminal (smartwatch), glasses-type terminal (smart glasses), HMD (head mounted display), etc.).

Of course, the terminal to which the present invention is applicable is not limited to the above described ones and may be interpreted to include all terminals which may communicate with external devices.

Further, the customer terminal 20 may be, e.g., a portable mobile wireless communication device examples of which may be interpreted to include navigation devices, a Personal Communication System (PCS), Global System for Mobile communications (GSM), Personal Digital Cellular (PDC), Personal Handyphone System (PHS), Personal Digital Assistant (PDA), International Mobile Telecommunication (IMT)-2000, Code Division Multiple Access (CDMA)-2000, W-Code Division Multiple Access (W-CDMA), Wireless Broadband Internet (WiBro) terminal, a smartphone, a smartpad, tablet PC, or any other various types of handheld wireless communication devices.

Figure 2:
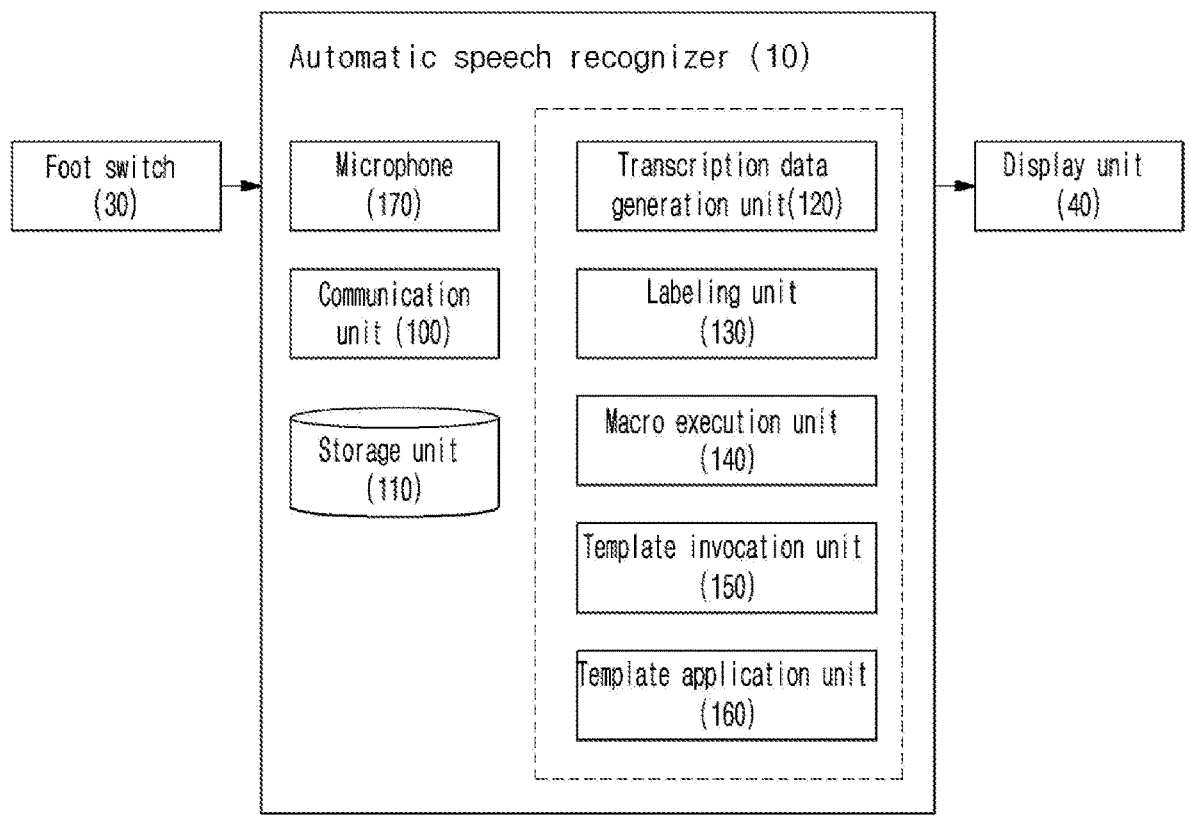
FIG. 2 is a block diagram illustrating a configuration of a medical automatic speech recognizer using a keyboard macro function according to an embodiment of the present invention.

FIG. 2 is a block diagram illustrating a configuration of an automatic speech recognizer using a keyboard macro function according to an embodiment of the present invention.

As shown in FIG. 2, according to an embodiment, an automatic speech recognizer 10 using a keyboard macro function receives speech data input through a microphone 170. The automatic speech recognizer 10 receives an on/off signal from a foot switch 30.

Further, the automatic speech recognizer 10 may display, through the display unit 40, necessary information on the screen by performing the operation requested by the speech data.

In this case, in displaying the information on the screen through the display unit 40, the automatic speech recognizer 10 may transcribe the recognized speech to a data inputtable space on various utility programs, such as a notepad, chatting program, HWP or Word, or Excel, as well as the electronic medical record (EMR) program, and output it in the form of text.

The automatic speech recognizer 10 may directly convert the speech-recognized content into text in such a manner as to be input by a virtual keyboard and output it on the screen, so that it is possible to output it on the screen as if it is directly input on the program by a keyboard.

Accordingly, it is possible to provide the advantage that the range of programs to which the transcribed content is applicable is increased in displaying the speech, recognized by the automatic speech recognizer 10, in the form of text.

Accordingly, the automatic speech recognizer 10 according to an embodiment may input the result, obtained via speech recognition on the input field, as if it is actually input by a keyboard, without separate interaction, if there is an input field regardless of the type of the EMR program in the medical industry.

Further, the automatic speech recognizer 10 may interwork with various imaging devices or medical devices. In other words, according to an embodiment, the automatic speech recognizer 10 may control the operation of the interworking imaging device or medical device according to the on/off control of the foot switch 30 or the speech data input through the microphone 170.

In an aspect, the foot switch 30 has an on/off control function. According to an embodiment, the automatic speech recognizer 10 is implemented so that the microphone 170 in the automatic speech recognizer is activated when one foot switch 30 is stepped on, and the microphone 170 is deactivated when the foot switch 30 is stepped off.

Conventionally, to activate the automatic speech recognizer 10, recording is activated by a built-in button in the microphone or the microphone is activated through a mouse click. According to the aspect of the present invention, in a context where the hands are difficult to use, a signal generated from the foot switch 30 is used as a trigger that is received by the program driven on the automatic speech recognizer 10 and activates the automatic speech recognizer 10, thus providing convenience. It may also be implemented to activate the microphone through a built-in button of the microphone or a mouse click according to the user's selection.

According to another embodiment, a plurality of foot switches 30 may be provided. If there are a plurality of foot switches 30, on-state switches 30 may be configured to perform different functions, e.g., line break or importing of stored template.

According to another embodiment, in a state in which the automatic speech recognizer 10 and the microphone 170 have been activated, the automatic speech recognizer 10 records and monitors the speech input through the microphone 170 in the form of sessions and, upon detecting a specific onset keyword, e.g., a preset keyword, such as "start recording," inputs the result, speech-recognized thereafter, through a macro-based input device.

In other words, it is implemented to display, on the display unit 40, the data transcribed by the keyword "start recording" in a manner of inputting with a keyboard.

On the other hand, upon detecting a specific end keyword ("end recording"), the automatic speech recognizer 10 records the result, speech-recognized thereafter, in the form of sessions and waits for detection of a specific onset keyword. In other words, the automatic speech recognizer 10 may be implemented not to display, on the display 40, the transcribed content despite speech recognition after recognizing a preset keyword meaning ending of recording, such as "end recording."

According to an aspect of the present invention, there may be provided an automatic speech input device in such a type as to transcribe the speech input through the automatic speech recognizer 10, which is always active, as text, to the input field of the recording system in the medical field, and input the transcribed text through the keyboard macro input device without a separate keyboard or mouse.

According to an embodiment, the automatic speech recognizer 10 using a keyboard macro function includes a communication unit 100, a storage unit 110, a transcription data generation unit 120, a labeling unit 130, a macro execution unit 140, a template invocation unit 150, and a template application unit 160.

The communication unit 100 may include both a communication module for supporting wired communication and a mobile communication module for supporting wireless communication. The mobile communication module transmits or receives wireless signals to/from at least one of a base station and an external terminal over a mobile communication network established as per mobile communication standards, protocols, or schemes, such as global system for mobile communication (GSM), code division multiple access (CDMA), CDMA2000, enhanced voice-data optimized or enhanced voice-data only (EV-EVDO), wideband CDMA (WCDMA), high speed downlink packet access (HSDPA), high speed uplink packet access (HSUPA), long term evolution (LTE), or LTE-advanced (LTE-A).

In an embodiment, the communication unit 100 performs data communication with the speech recognizer server 20. Information required in the process of generating transcription data based on the speech data input through the microphone may be received from the speech recognizer server 20.

Further, the communication unit 100 may perform communication with a medical measurement device or medical imaging device physically separated therefrom The communication unit 100 may receive medical data or image data from the medical measurement device or medical imaging device through wired communication or short-range wireless communication. Further, the communication unit 100 may transmit control signals to the medical measurement device or medical imaging device.

The storage unit 110 stores a program for generating transcription data based on the speech data. Here, the storage unit 110 collectively refers to a volatile storage device and a non-volatile storage device that continuously maintain stored information even when power is not supplied.

For example, the storage unit 110 may include NAND flash memory, such as a compact flash (CF) card, a secure digital (SD) card, a Memory Stick™, a solid-state drive (SSD), and a micro SD card, a magnetic computer storage device, such as hard disk drive (HDD), etc., and an optical disc drive, such as CD-ROM, DVD-ROM, etc.

In an embodiment, the storage unit 110 stores a program for generating transcription data and a labeling target word for performing a macro function from the transcription data. The labeling target word may be preset by the user.

The transcription data generation unit 120 generates transcription data based on the speech data input through the microphone 170 as the program stored in the storage unit 110 is executed.

In automatic speech recognition, since it is impossible to directly extract necessary information when the source data is speech, the transcription data generation unit 120 needs to perform a transcription process of converting the character string of the speech data input through the microphone 170.

In an embodiment, the transcription data generation unit 120 may generate transcription data in a text format.

If the transcription data generated by the transcription data generation unit 120 includes a preset labeling target word to perform a macro function, the labeling unit 130 labels the generated transcription data, sessionizes it, and stores it in the storage unit 110.

The labeling unit 130 determines whether the transcription data includes a labeling word target word for performing a macro function.

The labeling target word is preset by the user or a service provider. For example, the labeling target word is implemented as a keyword, such as "capture area", "capture position", "capacity", "show me", "line break", or "open a parenthesis". In other words, the labeling target word may be a keyword for performing a macro function.

For example, if the speech data "This capture position is the ascending colon" is input through the microphone 170, the labeling unit 130 labels "capture position" and may store it in the session.

In this case, the labeling unit 130 labels and stores the capture data input from the medical capture device together with the capture position input as the speech for the labeling of "capture position". The capture data may be, e.g., an image or video file captured by an ultrasound or MRI technique.

In an auxiliary aspect, when the user inputs a keyword, the labeling unit 130 may determine the word relevance from the inputted keyword, grasp a range of meanings with medical terminology-considered ontology logic, and limit the keyword search range to the range of meanings. Accordingly, it is possible to achieve higher-accuracy speech recognition in the process of transcribing and processing speech data.

In other words, according to an embodiment, the automatic speech recognizer 10 using a keyboard macro function may convert the speech data input through the microphone 170 into a text form and hold it like a session. Therefore, the automatic speech recognizer 10 may serve as an auxiliary recording device that records and memorizes the current context even when use of the hands is difficult due to the characteristics of the medical environment.

For example, if information, such as the patient's name or treatment code, is input after a previously agreed code is input as speech through the microphone, it may be added, as identification code, to the transcription data recently sessionized and stored by the labeling unit 130.

If a preset labeling target word is included in the transcription data generated by the transcription data generation unit 120, the macro execution unit 140 may invoke the transcription data, sessionized by the labeling unit 130, and performs operation according to the macro (macro instruction) function.

In other words, if a labeling word configured to perform the macro function on the transcription data is input, the macro execution unit 140 may perform the function set to perform accordingly.

For example, if the speech data "tell me the capture position" is input, information related to the "capture position" among the record contents sessionized and stored by the labeling unit 130 may be provided to be differentiated as visual data by being highlighted. Further, it is also possible to feed back information regarding data regarding the capture position through speech.

It is also possible to further provide a capture image or capture image information from the medical imaging device, which has been matched and stored with the labeling information "capture position."

For example, upon recognition the speech "image capture, passed through the transverse colon, and now enters the ascending colon," the transcription data generation unit 120 may convert the speech into transcription data, and the macro execution unit 140 may recognize the labeling "image capture" and store the image, captured by the medical imaging device, together with the recognized transcription data.

Thereafter, upon recognizing the speech "image search, from transverse colon to ascending colon," the transcription data generation unit 120 may convert the speech into transcription data, and the macro execution unit 140 may recognize the label "image search" and extract the data recognized as the capture data for the corresponding portion by the medical imaging device from the stored information and provide the extracted data as the result of the search.

In an aspect, the template invocation unit 150 invokes a preset sentence template of transcription data according to the macro function. The format of the sentence template is not limited to any one format. The format of the sentence template may be implemented not only in the format of a single sentence but also in a format including a plurality of sentences.

For example, if speech data, such as "invoke the first template" or "import the first template," is input, the template invocation unit 150 may import a template sentence designated as the first template in a stored template list.

Here, the template invocation unit 150 may invoke the template in such a manner as to import content recorded in a remote template server which is a remote storage medium. In other words, various, updatable template forms may be used.

In this case, the templates may be identified by serial numbers or contextual keywords. The identification information, i.e., serial number or contextual keyword, for identifying the template may be preset by the user.

In this case, the template sentence invoked by the template invocation unit 154 may be output n the form of speech or may be output in a visual form on the screen.

The template application unit 160 receives the variable value of the sentence template invoked based on the speech data input through the microphone 170 and applies it.

The user may input the variable value by speech while identifying the template sentence invoked by the template invocation unit 150, output in a visual form on the screen or output in the form of speech.

For example, if the template sentence invoked by the template invocation unit 150 is "after injecting cimetropium 1) _____ 2) spray lidocaine for pharyngeal anesthesia," the user may input, through the microphone 170, the speech "first variable value 5 mg" and "second variable value 10%" to thereby modify the content of the template sentence or newly input the variable values.

In other words, it is possible to provide convenience in inputting medical records or surgery process by entering only variable values, which are changeable depending on patients after a medical examination, to a preset template sentence for a repeatable context.

In this case, various changes or modifications may be made to inputting the variable values of the template sentence invoked by the template invocation unit 150.

The template application unit 160 applies the input variable to thereby generate a new template sentence and provides the new template sentence to the labeling unit 130 or the macro execution unit 140 to be sessionized and stored or to perform operations according thereto.

In other words, the macro execution unit 140 may use the variable value-applied transcription data to perform the operation necessary according to the function, or the labeling unit 130 may recognize it as new data and sessionize and store it.

According to an additional aspect of the present invention, the automatic speech recognizer 10 according to an embodiment further includes a foot switch 30 having an on/off control function.

The transcription data generation unit 120 generates transcription data based on the speech data input through the microphone 170 when the foot switch 30 is in an ON state.

According to this aspect, in a context where the hands are difficult to use, a signal generated from the foot switch 30 is used as a trigger that is received by the program driven on the automatic speech recognizer 10 and activates the automatic speech recognizer 10, thus providing convenience.

Further, a plurality of foot switches 30 may be provided. When there are a plurality of foot switches 30, the foot switches 30 may be implemented to perform the function of, e.g., line break of the input or importing a stored template depending on the type and number of the foot switches which are switched on.

For example, in a case where there are foot switches a, b, and c, if foot switch a is in an ON state, transcription data is generated from speech data input through the microphone, if only foot switch b is in an ON state, transcription data is generated from the speech data input through the microphone and is stored as it is, and if only foot switch c is in an ON state, the automatic speech recognizer 10 may be operated in the template invocation mode.

If foot switches a and b are simultaneously in the ON state, the automatic speech recognizer 10 may return to the initial state. The function performed according to the control of the foot switch 30 is not limited thereto, but various modifications may be made thereto. In other words, use of the plurality of foot switches 30 enables input of more various control signals even without performing input with a hand.

According to an aspect of the present invention, the medical automatic speech recognizer using a keyboard macro function may further include an artificial intelligence module.

The artificial intelligence (AI) module may perform various functions requested by the speech data input through the microphone 170. Further, the artificial intelligence module may include a deep learning training module and may be implemented to self-learn the operation according to speech recognition by training. According to an embodiment, the artificial intelligence module may additionally provide, through a web search, information necessary according to the transcription data recognized by speech.

Figure 3:
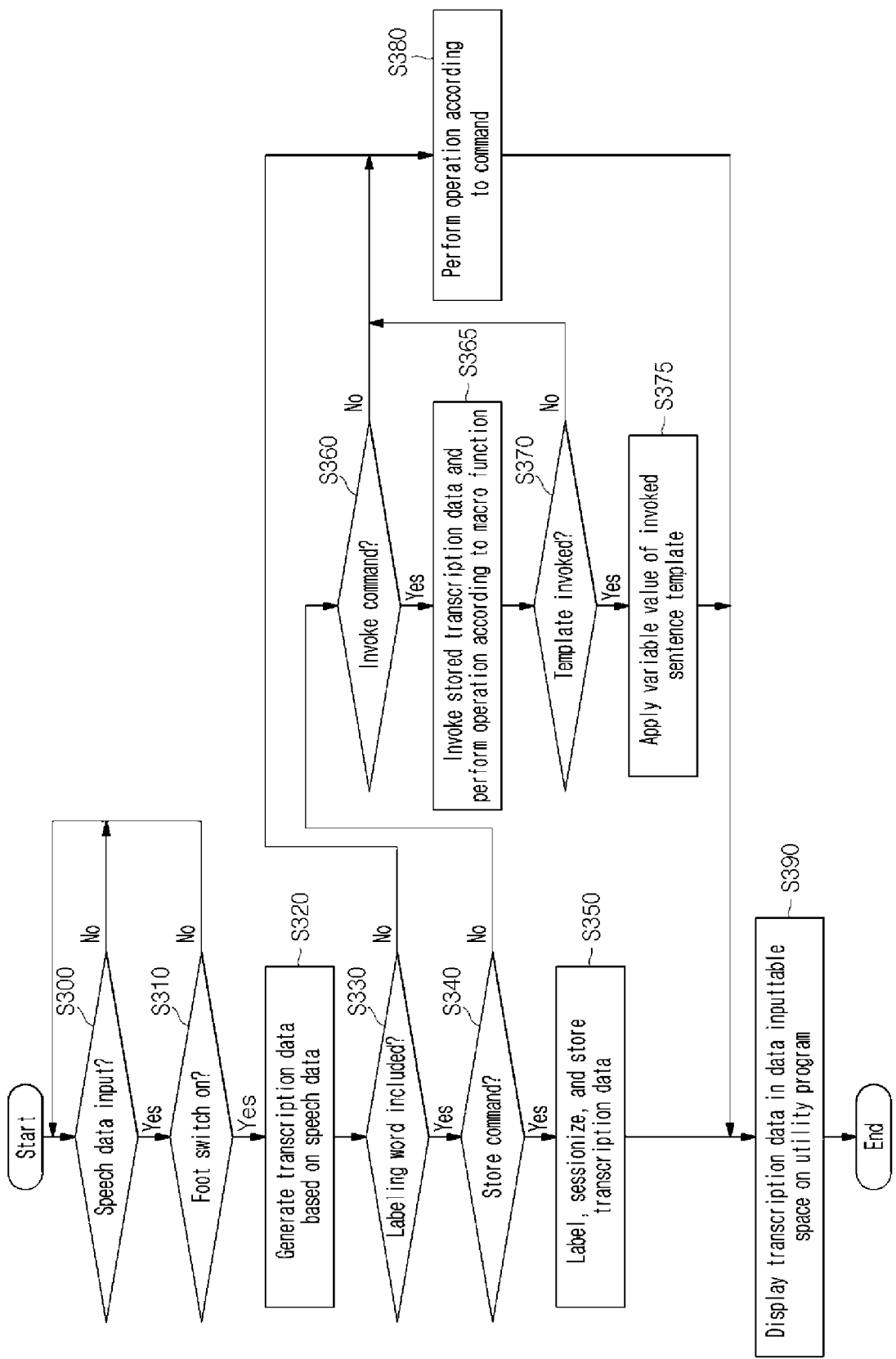
FIG. 3 is a flowchart illustrating a medical automatic speech recognition method using a keyboard macro function according to an embodiment of the present invention.

FIG. 3 is a flowchart illustrating a medical automatic speech recognition method using a keyboard macro function according to an embodiment of the present invention.

In a medical automatic speech recognition method performed by a medical automatic speech recognizer using a keyboard macro function, if speech data is input through the microphone (S300), the transcription data generation unit generates transcription data based on the speech data input through the microphone (S320).

In this case, the step of generating the transcription data generates the transcription data based on the speech data input through the microphone, when the foot switch with an on/off control function is in an ON state (S310).

According to this aspect, in a context where the hands are difficult to use, a signal generated from the foot switch is used as a trigger that is received by the program driven on the medical automatic speech recognizer and activates the automatic speech recognizer, thus providing convenience.

If the transcription data generated by the transcription data generation unit includes a preset labeling target word for performing the macro function (S330), the labeling unit labels the generated transcription data, sessionizes and stores it (S340 and S350).

The labeling unit determines whether the transcription data includes a labeling word target word for performing a macro function.

The labeling target word is preset by the user or a service provider. For example, the labeling target word is implemented as a keyword, such as "capture area", "capture position", "capacity", or "show me". In other words, the labeling target word may be a keyword for performing a macro function.

For example, if the speech data "This capture position is the ascending colon" is input through the microphone, the labeling unit labels "capture position" and may store it in the session.

In other words, the speech data input through the microphone may be converted into a text form that may then be held like a session. Therefore, the automatic speech recognizer 10 may serve as an auxiliary recording device that records and memorizes the current context even when use of the hands is difficult due to the characteristics of the medical environment.

On the other hand, if a preset labeling target word is included in the transcription data generated by the transcription data generation unit, the macro execution unit invokes the transcription data, sessionized and stored in the session-izing and storing step, and performs operation according to the macro function (S360 and S365).

According to an embodiment, if a labeling word configured to perform the macro function on the transcription data is input, the macro execution unit may perform the function set to perform accordingly.

For example, if the speech data "tell me the capture position" is input, information related to the "capture position" among the record contents sessionized and stored by the labeling unit 130 may be provided as visual data by being highlighted. Further, it may be fed back through speech.

In an aspect of the present invention, if the template invocation unit invokes a preset sentence template of transcription data according to the macro function (S370), the template application unit receives and applies the variable value of the sentence template invoked based on the speech data input through the microphone (S375).

For example, if speech data, such as "invoke the first template" or "import the first template," is input, the template invocation unit may import a template sentence designated as the first template in a stored template list.

In this case, the templates may be identified by serial numbers or keywords for some contexts.

The template sentence invoked by the template invocation unit may be output in the form of speech or may be output in a visual form on the screen.

The template application unit receives and applies the variable value of the sentence template invoked based on the speech data input through the microphone.

The user may input the variable value while identifying the template sentence invoked by the template invocation unit, output in a visual form on the screen or output in the form of speech.

For example, if the template sentence invoked by the template invocation unit is "after injecting cimetropium 1) _____ 2) spray lidocaine for pharyngeal anesthesia," the user may input "first one 5 mg" and "second one 10%" as variable values to thereby modify the content of the template sentence or newly input the variable values. Various changes or modifications may be made to inputting the variable values of the invoked template sentence.

The template application unit applies the input variable to thereby generate a new template sentence and provides the new template sentence to the labeling unit or the macro execution unit to be sessionized and stored or to perform operations according thereto.

Additionally, according to the medical automatic speech recognition method using a keyboard macro function according to an embodiment, the medical automatic speech recognizer may perform the operation according to a normal speech data command not including a labeling word (S380).

Thereafter, the automatic speech recognizer performs the operation requested by speech data, thereby displaying necessary information on the screen.

In this case, in displaying the information on the screen through the display unit, the automatic speech recognizer may transcribe the recognized speech to a data inputtable space on various utility programs, such as a notepad, chatting program, HWP or Word, or Excel, as well as the electronic medical record (EMR) program, and output it in the form of text (S390).

The automatic speech recognizer 10 may directly convert the speech-recognized content into text in such a manner as to be input by a virtual keyboard and output it on the screen, so that it is possible to output it on the screen as if it is directly input on the program by a keyboard.

The above-described method may be implemented as an application or in the form of program commands executable through various computer components, which may then be recorded in a computer-readable recording medium. The computer-readable medium may include programming commands, data files, or data structures, alone or in combinations thereof.

The programming commands recorded in the computer-readable medium may be specially designed and configured for the present invention or may be known and available to one of ordinary skill in the computer software industry.

Examples of the computer readable recording medium may include, but is not limited to, magnetic media, such as hard disks, floppy disks or magnetic tapes, optical media, such as CD-ROMs or DVDs, magneto-optical media, such as floptical disks, memories, such as ROMs, RAMs, or flash memories, or other hardware devices specially configured to retain and execute programming commands.

Examples of the programming commands may include, but are not limited to, high-level language codes executable by a computer using, e.g., an interpreter, as well as machine language codes as created by a compiler. The above-described hardware devices may be configured to operate as one or more software modules to perform processing according to the present invention and vice versa.

The invention claimed is:

1. An automatic speech recognition method using a keyboard macro function, performed on an automatic speech recognizer using the keyboard macro function, comprising the steps of:

generating transcription data based on speech data input through a microphone by a transcription data generation unit when a plurality of foot switches having an on/off control function is an ON state, wherein the foot switches are implemented to perform the function of line break of the input or importing a stored template depending on the type and number of the foot switches which are switched on; and labeling, sessionizing and storing the generated transcription data if the generated transcription data includes a preset labeling target word for performing a macro function, by a labeling unit, wherein information related to the labeling target word is extracted from the recorded contents that are labeled, sessionized, and stored and is provided to be differentiated as visual data, wherein the method further comprising the steps of invoking, by a template invocation unit, a preset sentence template of transcription data according to the macro function; and receiving and applying, by a template application unit, a variable value of the sentence template, invoked based on the speech data input through the microphone, wherein when the speech data containing contextual keywords preset by the user is input, sentence templates identified by contextual keywords are imported from a stored template list or content recorded on a remote template server.

2. The automatic speech recognition method of claim 1, further comprising the step of displaying the generated transcription data by displaying the generated transcription data in a data inputtable space on a utility program in a manner of being input by a virtual keyboard.

3. The automatic speech recognition method of claim 1, further comprising the step of invoking the transcription data, sessionized and stored in the sessionizing and storing step, and performing, by macro execution unit, an operation according to the macro function if the generated transcription data includes the preset labeling target word.

4. An automatic speech recognizer using a keyboard macro function, comprising:

a transcription data generation unit generating transcription data based on speech data input through a microphone when a plurality of foot switches having an on/off control function is an ON state, wherein the foot switches are implemented to perform the function of line break of the input or importing a stored template depending on the type and number of the foot switches which are switched on;

a labeling unit labeling, sessionizing and storing the generated transcription data if the transcription data generated by the transcription data generation unit includes a preset labeling target word for performing a macro function wherein information related to the labeling target word is extracted from the recorded contents that are labeled, sessionized, and stored and is provided to be differentiated as visual data; and a template invocation unit invoking a preset sentence template of transcription data according to the macro function; and a template application unit receiving and applying a variable value of the sentence template invoked based on the speech data input through the microphone, wherein when the speech data containing contextual keywords preset by the user is input, sentence templates identified by contextual keywords are imported from a stored template list or content recorded on a remote template server.

5. The automatic speech recognizer of claim 4, further comprising a display unit displaying the transcription data, generated by the transcription data generation unit, in a data inputtable space on a utility program in a manner of being input by a virtual keyboard.

6. The automatic speech recognizer of claim 4, further comprising a macro execution unit invoking the transcription data, sessionized by the labeling unit, and performing an operation according to the macro function if the transcription data generated by the transcription data generation unit includes the preset labeling target word.

* * * * *